United States Patent
Williams

(10) Patent No.: US 8,241,606 B2
(45) Date of Patent: *Aug. 14, 2012

(54) SYNTHESIS OF A RADIOFLUORINATED PEPTIDE USING PHOTOLABILE PROTECTING GROUPS

(75) Inventor: Lorenzo Williams, Oslo (NO)

(73) Assignee: GE Healthcare AS, Oslo (NO)

( * ) Notice: Subject to any disclaimer, the term of this patent is extended or adjusted under 35 U.S.C. 154(b) by 374 days.

This patent is subject to a terminal disclaimer.

(21) Appl. No.: 12/518,279

(22) PCT Filed: Dec. 18, 2007

(86) PCT No.: PCT/NO2007/000448
§ 371 (c)(1), (2), (4) Date: Jun. 9, 2009

(87) PCT Pub. No.: WO2008/075966
PCT Pub. Date: Jun. 26, 2008

(65) Prior Publication Data
US 2010/0022746 A1 Jan. 28, 2010

Related U.S. Application Data

(60) Provisional application No. 60/870,462, filed on Dec. 18, 2006.

(51) Int. Cl.
*A61K 51/00* (2006.01)
(52) U.S. Cl. ............................ 424/1.69; 424/1.89
(58) Field of Classification Search .................. 530/300, 530/317, 329; 424/1.11, 1.69, 1.89
See application file for complete search history.

(56) References Cited

U.S. PATENT DOCUMENTS

| 2010/0016551 A1 | 1/2010 | Williams |
| 2010/0068139 A1 | 3/2010 | Cuthbertson et al. |

FOREIGN PATENT DOCUMENTS

| WO | 2006/024722 | 3/2006 |
| WO | 2006/030291 | 3/2006 |

OTHER PUBLICATIONS

Nyeki, et.al. "Synthesis of Angiotensin II Antagonists with Variations in Position 5" Journal of Medicinal Chemistry, American Chemical Society, Wash. US, vol. 30, Jan. 1987, pp. 1719-1724.
Yang, et.al. "Synthesis of Chiral [beta]<3>-aminoxy peptides" Journal of Organic Chemistry 20041029 US, vol. 69, No. 22, Oct. 29, 2004, pp. 7577-7581.
Pillai, "Photoremovable protecting groups in organic synthesis" Synthesis, Georg Thieme Verlag, Stuttgart, DE, vol. 1, No. 1, Jan. 1, 1980, pp. 1-26.
Theodoridis, "Nitrogen protecting groups: recent developments and new applications" Tetrahedron, Elsevier Science Publishers, Amsterdam, NL, vol. 56, No. 16, Apr. 1, 2000, pp. 2339-2358.
Bochet "Photolabile protecting groups and linkers" J. Chem. soc., Perkin Trans. 1 2002, pp. 125-142.

*Primary Examiner* — Michael G Hartley
*Assistant Examiner* — Jagadishwar Samala

(57) ABSTRACT

The present invention encompasses a method of preparing a radiofluorinated compound by adding a photolabile protecting group, R, to an aminoxy group of a peptide based compound wherein the peptide based compound reacts with a light of a specified wavelength in an automated radiosynthesis apparatus to form a radiofluorinated compound. The present invention further relates to a photolabile peptide based compound.

15 Claims, No Drawings

SYNTHESIS OF A RADIOFLUORINATED PEPTIDE USING PHOTOLABILE PROTECTING GROUPS

This application is a filing under 35 U.S.C. 371 of international application number PCT/NO2007/000448, filed Dec. 18, 2007, which claims priority to application No. 60/870,462 filed Dec. 18, 2006, in The United States the entire disclosure of which is hereby incorporated by reference.

FIELD OF THE INVENTION

The present invention encompasses a method of preparing a radiofluorinated compound by adding a photolabile protecting group, R, to an aminoxy group of a peptide based compound wherein the peptide based compound reacts with a light of a specified wavelength in an automated radiosynthesis apparatus to form a radiofluorinated compound. The present invention further relates to a photolabile peptide based compound.

BACKGROUND OF THE INVENTION

The application of radiolabelled bioactive peptides for diagnostic imaging is gaining importance in nuclear medicine. Biologically active molecules, which selectively interact with specific cell types, are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of approximately 110 minutes, is the positron-emitting nuclide of choice for many receptor-imaging studies. Therefore, $^{18}$F-labelled bioactive peptides have great clinical potential because of their utility in PET to quantitatively detect and characterise a wide variety of diseases.

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes that break down the proteins of the basement membrane, as well as inhibitors that limit the action of these potentially harmful enzymes. The other prominent effect of angiogenic factors is to cause endothelial cells to migrate and divide. Endothelial cells that are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodelling of tissues, including wound healing and inflammatory processes. Tumours must initiate angiogenesis when they reach millimeter size in order to keep up their rate of growth. Angiogenesis is accompanied by characteristic changes in endothelial cells and their environment. The surface of these cells is remodelled in preparation for migration, and cryptic structures are exposed where the basement membrane is degraded, in addition to the variety of proteins, which are involved in effecting and controlling proteolysis. In the case of tumours, the resulting network of blood vessels is usually disorganised, with the formation of sharp kinks and also arteriovenous shunts. Inhibition of angiogenesis is also considered to be a promising strategy for antitumour therapy. The transformations accompanying angiogenesis are also very promising for diagnosis, one example being malignant disease, but the concept also shows great promise in inflammation and a variety of inflammation-related diseases, including atherosclerosis, the macrophages of early atherosclerotic lesions being potential sources of angiogenic factors.

Many ligands involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

The efficient targeting and imaging of integrin receptors associated with angiogenesis in vivo demands therefore a selective, high affinity RGD based vector that is chemically robust and stable. Furthermore, the route of excretion is an important factor when designing imaging agents in order to reduce problems with background.

WO 03/006491 describes peptide-based compounds, which target integrin receptors associated with angiogenesis. International application WO2004/080492 describes methods suitable for labelling biologically active vectors with $^{18}$F and WO2006/030291 describes peptide-based compounds having utility for diagnostic imaging which may be prepared rapidly. One difficulty, however, remains is obtaining a stable and a more efficient method for synthesizing these peptide compounds in an automated radiosynthesis apparatus. The current invention sets forth herein the use of light at a specified wavelength to improve the efficiency, stability and the avoidance of corrosive reagents such as trifluoroacetic acid or hydrochloric acid of the peptide-based compounds that are utilized for PET imaging.

Discussion or citation of a reference herein shall not be construed as an admission that such reference is prior art to the present invention.

SUMMARY OF THE INVENTION

Photolabile protecting groups (PPG) are found in many important applications in synthetic and biomedical chemistry. From a synthetic point of view, PPGs allow for an orthogonal protecting group strategy since they do not require reagents and/or heating for their removal. Hence, there is a novel advantage for using PPGs in peptide based compounds. For biomedical applications PPGs provide the spatial and temporal control of the release of bio-active substrates.

In general, there are drawbacks associated with utilizing protecting groups in peptide based compounds. In addition to the fact that their introduction and cleavage require at least two synthetic steps and thus time, they complicate a synthetic plan by their incompatibility with many organic reagents. The complication increases rapidly if a number of different protecting groups are on the same molecule. Photolabile protecting groups, however, don't require any reagent for their cleavage, just light. This category of protecting groups open the possibility of dealing with extremely sensitive and complex molecules such as peptide based compounds and more specifically radiofluorinated peptide based compounds used in angiogenesis that may otherwise be incompatible with acids or bases for instance.

Furthermore, in general, the photolabile protecting group moiety can be tailored to match light of a preferred wavelength if desired. Ideally to effect photolysis rapidly one would want a photolabile moiety that gives a high quantum yield at a specific wavelength. Wavelengths in the range of about 200 nanometers to about 600 nanometers are suitable to effect deprotection, but more preferably the wavelength range is from about 220 nanometers and 380 nanometers where optimum quantum yields in the present invention are yielded.

DETAILED DESCRIPTION OF THE INVENTION

The present invention encompasses a method of preparing a radiofluorinated compound via a photolabile protecting group strategy. The photolabile protecting group, R, is attached to an aminoxy group of a linker attached to a vector, e.g. a targeting peptide. It can be readily cleaved by irradiating with light of an optimum wavelength to liberate the aminoxy functionality which can then be conjugated to an $^{18}$F-synthon in an automated radiosynthesis apparatus to form a radiofluorinated compound. Downstream processing is facilitated since this form of deprotection does not use any reagents.

The automated radiosynthesis apparatus utilized herein is designed to streamline Positron Emission Tomography (PET) radiopharmaceutical production. In general, an automated radiosynthesis apparatus features a single-use cassette system that accommodates different chemistries to facilitate the production of multiple PET tracers. PET imaging is limited by both the infrastructure and expertise required for producing radiopharmaceuticals. With the utilization of an automated radiosynthesis apparatus, all chemicals necessary to produce radiochemical PET imaging agents or tracers are preloaded in the exact quantities onto the single-use cassette. The user simply installs the cassette and pushes a button. Then, a cyclotron, which is an accelerator in which charged particles are propelled by an alternating electric field in a constant magnetic field, delivers an aqueous solution containing radioactive $^{18}$F-fluoride through a tube to the system. A light source such as medium or high pressure Hg or Hg—Xe lamps fitted with filters can be directly attached to the apparatus. In a certain period, preferably about 18-28 minutes and more preferably about 23 minutes, the radiochemical PET imaging agent has been synthesized. The progress of the synthesis can be tracked on an accompanying computer. After synthesis, the program performs a rinsing cycle; after removing the cassette, the system is available for the next run.

The light used herein is generally produced from lamps. These lamps are generally medium or high pressure Hg or Hg—Xe lamps fitted with filters (e.g. Vycor™, Pyrex™) to direct light of a desired wavelength.

The light source is either present in the reactor vessel or the reactor vessel should be transparent so that light can enter the vessel. An advantage of using a light source herein is that the light source can be optionally used as an external source and thus does not have to be integrated into the automated radiosynthesis apparatus. Light lamps are an example of a light source that is used in the present invention. Light lamps tend to get quite hot and can be cooled if necessary by applying a water jacket to the unit. This is not necessary though in the current invention since the reaction time is quick, less than 6 minutes, preferably about 3 minutes and more preferably about 45-60 seconds.

There are further various advantages of utilizing light to prepare a radiofluorinated compound in an automated radiosynthesis apparatus. One of those advantages is that no reagents are used in the synthetic step thus avoiding the use of corrosive trifluoroacetic acid or hydrogen chloride. A further advantage of using this invention is stabilizing an aminoxy precursor to efficiently obtain a radiofluorinated compound in an automated radiosynthesis apparatus.

One embodiment of the present invention encompasses a method of preparing a compound of formula (II) comprising the steps;
(i) adding a photolabile protecting group, R, to an aminoxy group to give formula (I)

(I)

wherein the R group in (I) is $CO_2Bn(CBz)$, $CH_2C_6H_4$-m-$NO_2$, $CO_2C_26H_4$-m-$NO_2$, $CO_2CH(Ph)C_6H_4$-o-$NO_2$, $SO_2Bn$, $CO_2C(Me)_2$-3,5-$(MeO)_2C_6H_3$, or $CO_2CH_2$-3,5-$(MeO)_2C_6H_3$ wherein Bn denotes benzyl group, CBz denotes benzyloxycarbonyl group, Ph denotes a phenyl
(ii) illuminating compound (I) with a light of a specified wavelength in an automated radiosynthesis apparatus to form a compound of formula (II),

(II)

A vector used herein is a fragment of a compound or moiety having affinity for a receptor molecule, preferably a peptidic species or more preferably an angiogenesis targeting species such as an RGD peptide. A specific example of a vector used herein is an Arg-Gly-Asp peptide or an analogue thereof. An example of such a vector used herein comprises the fragment

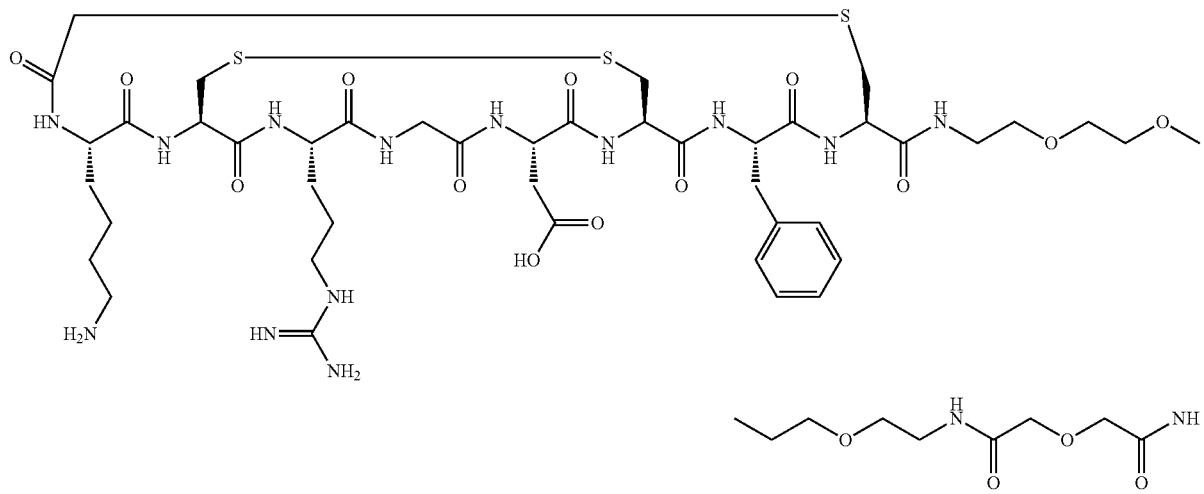

wherein a linker would be attached to the lysine amino group and said linker is:

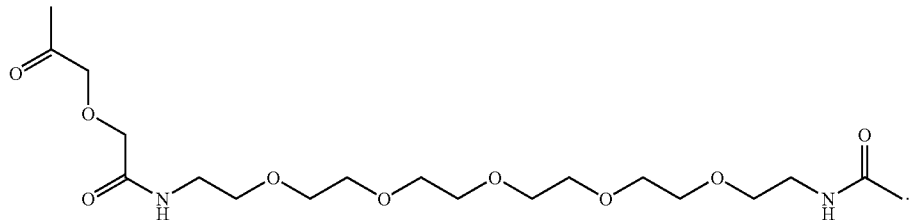

A further embodiment of the present invention depicts a method of preparing compounds (I) and (II) wherein the vector of compound (I) and (II) is a peptide based vector.

Another embodiment of the present invention depicts the compounds of (I) and (II) wherein the vector of compound (I) and (II) is an RGD-based peptide having affinity for angiogenesis.

Yet a further embodiment of the present invention depicts a method of preparing a radiofluorinated compound wherein the linker in compound (I) or compound (II) is based on a PEG building block.

The linker group in the compounds (I) and (II) have been chosen to provide good in vivo pharmacokinetics, such as favourable excretion characteristics in the resultant end product. The term linker as used herein means a moiety that links together a plurality of other moieties. The use of linker groups with different lipophilicities and/or charge can significantly change the in vivo pharmacokinetics of the peptide to suit the diagnostic need. For example, where it is desirable for a conjugate of compound (III) to be cleared from the body by renal excretion, a hydrophilic linker is used, and where it is desirable for clearance to be by hepatobiliary excretion a hydrophobic linked is used. A wide variety of linkers may be used, including biodegradeable linkers and biopolymers. The linker is at its simplest a bond between the vector and the aminoxy group or the 18F containing moiety. More generally, the linker will provide a mono- or multi-molecular skeleton, e.g. a linear, cyclic, or branched skeleton. The linker may further have the role to distance the vector from the reporter. The linker may comprise amino acids, or elements of such. Further, the linker may include structural type polysaccharides, storage-type polysaccharides, polyamino acids and methyl and ethyl esters thereof, and polypeptides, oligosaccharides and oligonucleotides. The linker may also comprise macromolecular structures such as dextran and preferably poly(ethyleneglycols), referred to as PEGs. Linkers including a PEG moiety have been found to slow blood clearance which is desirable in some circumstances. The linker may be derived from glutaric and/or succinic acid and/or a polyethyleneglycol based moiety.

Still a further embodiment of the present invention shows a method wherein compound (II) is reacted with an $^{18}$F-fluoride synthon, wherein the synthon is $^{18}$F radiolabelled benzaldehyde to prepare compound (III)

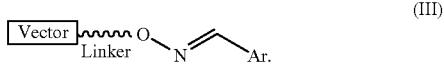

(III)

wherein Ar denotes an aryl function of the formula

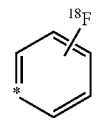

and * denotes the attachment to the imino function. Preferably the 18F radiolabel is in the para-position.

An additional embodiment of the invention depicts a method for preparing compound (III) wherein the $^{18}$F-fluoride synthon attached to compound (III) is $^{18}$F-radiolabelled benzaldehyde. Other examples of relevant $^{18}$F-fluoride synthons are provided in WO2004/080492, which is incorporated by reference.

A further embodiment of the invention shows a method of synthesis wherein compound (I) is of formula (IV)

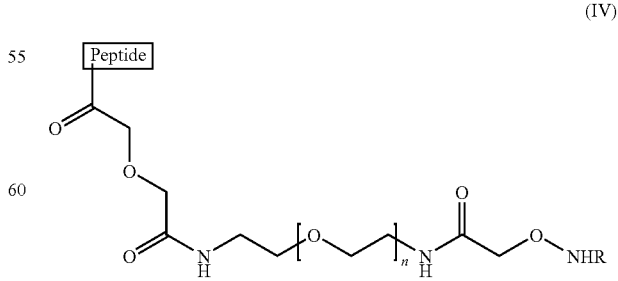

(IV)

wherein n=3-5 and n is preferably 5, wherein the peptide denotes

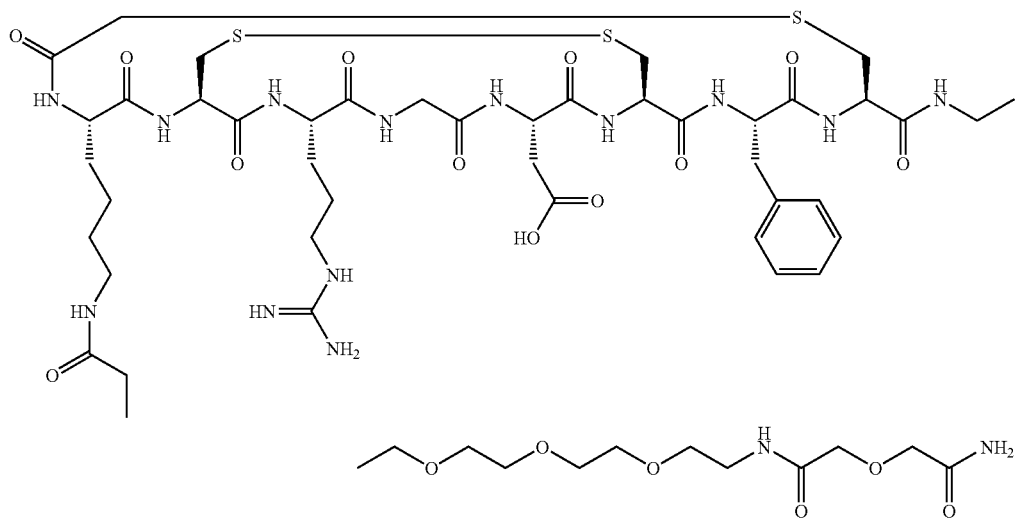

and R denotes $CO_2Bn(CBz)$, $CH_2C_6H_4$-m-$NO_2$, $CO_2C_26H_4$-m-$NO_2$, $CO_2CH(Ph)C_6H_4$-o-$NO_2$, $SO_2Bn$, $CO_2C(Me)_2$-3,5-$(MeO)_2C_6H_3$, or $CO_2CH_2$-3,5-$(MeO)_2C_6H_3$, wherein Bn denotes benzyl group, CBz denotes benzyloxycarbonyl group, and Ph denotes a phenyl.

Yet another embodiment of the invention presents a method according to (i) adding a photolabile protecting group, R, to an aminoxy group to give formula (I)

wherein the R group in (I) is $CO_2Bn(CBz)$, $CH_2C_6H_4$-m-$NO_2$, $CO_2C_26H_4$-m-$NO_2$, $CO_2CH(Ph)C_6H_4$-o-$NO_2$, $SO_2Bn$, $CO_2C(Me)_2$-3,5-$(MeO)_2C_6H_3$, or $CO_2CH_2$-3,5-$(MeO)_2C_6H_3$ wherein Bn denotes benzyl group, CBz denotes benzyloxycarbonyl group, and Ph denotes a phenyl (ii) illuminating compound (I) with a light of a specified wavelength in an automated radiosynthesis apparatus to form a compound of formula (II),

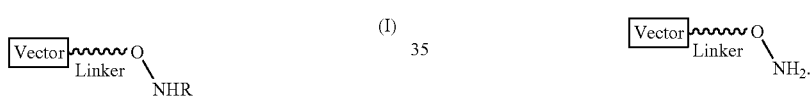

or preparing a compound of formula (V)

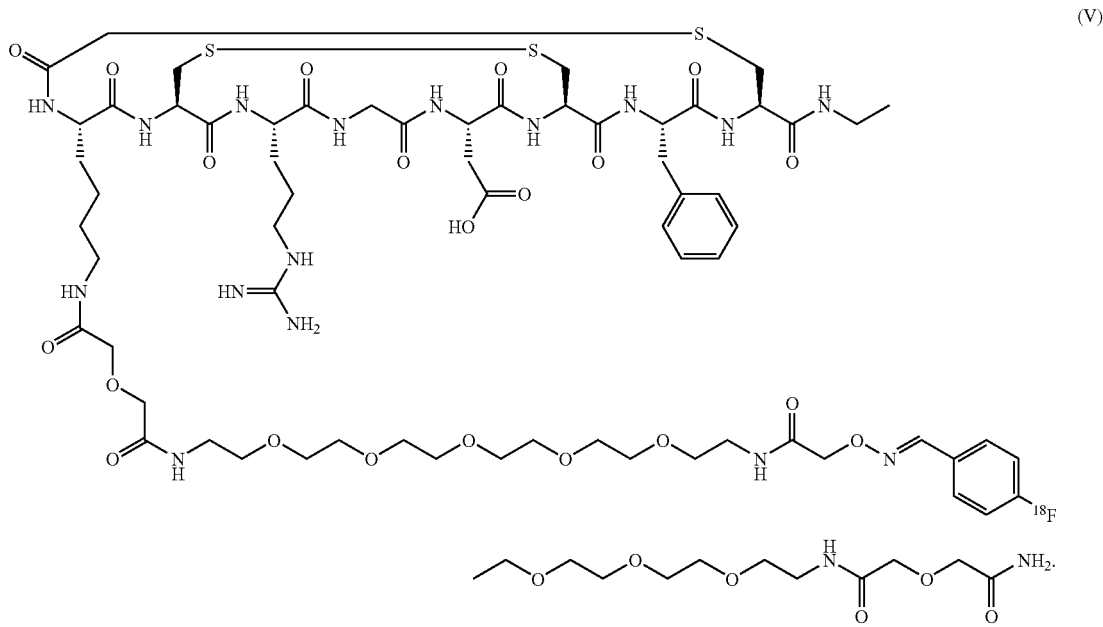

Still another embodiment of the invention shows a compound of (I). Yet another embodiment of the invention presents compound (I) or compound (II) wherein the vector is Arg-Gly-Asp peptide or an analogue thereof.

A further embodiment of the invention shows compound (I) or compound (II) wherein the vector comprises the fragment

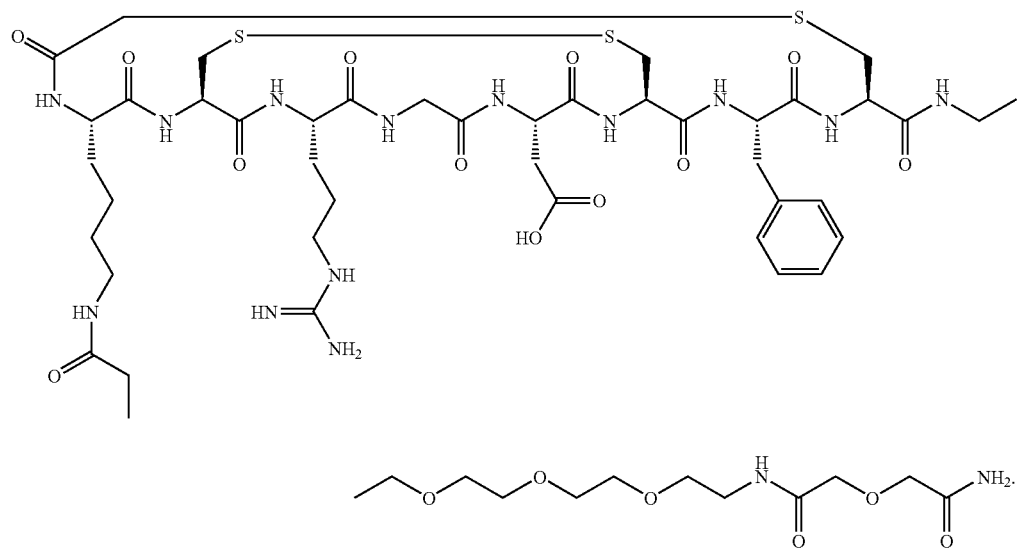

Another embodiment of the invention shows a method wherein the light of a specified wavelength from about 200 nm to about 600 nm is employed to liberate the aminoxy precursor and more preferably about 220 nm to about 380 mn as defined above.

Yet another embodiment of the invention depicts a method wherein the light used herein is produced from lamps.

Still another embodiment of the invention presents the lamps as being of medium or high pressure Hg or Hg—Xe lamps fitted with filters to direct light of the desired wavelength.

Another embodiment of the invention denotes compounds of formula (I) or wherein R is CO$_2$Bn (CBz) wherein Bn and CBz have the meanings above. This CO$_2$Bn (CBz) group attached to the aminoxy group (—ONH—) is a preferred group to be used herein.

EXAMPLES

The invention is further described in the following examples, which is in no way intended to limit the scope of the invention.

The invention is illustrated by way of examples in which the following abbreviations are used:
nm: nanometer
HPLC: high performance liquid chromatography
NMR: nuclear magnetic resonance
h$^v$: light at a specified wavelength.
hr(s): hour(s)
min(s): minute(s)
Bn: benzyl group
CBz: benzyloxycarbonyl group
Ph: phenyl
Me: methyl
DMAP: 4-(dimethylamino)pyridine
THF: tetrahydrofuran
DCM: dichloromethane
DMF: N,N-dimethylformamide
TBAF: tetrabutylammonium fluoride
MeOH: methanol
TLC: thin layer chromatography
TIS: triisopropylsilane
DMSO: dimethylsulphoxide
PBS: phosphate buffered saline
PyAOP: [7-azabenzotriazol-1-yloxytris(pyrrolidino)phosphonium-hexafluorophosphate]
Boc: —COOCH(CH$_3$)$_3$
RT: room temperature
SPE: solid phase extraction
m: meta position
o: ortho position

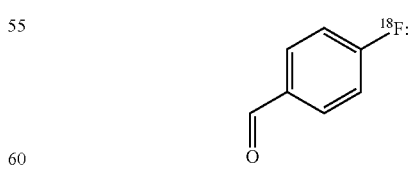

4-$^{18}$F-benzaldehyde

Preparation of a Peptide Precursor (Compound 2)

The peptide, compound 2 was synthesized using standard peptide synthesis.

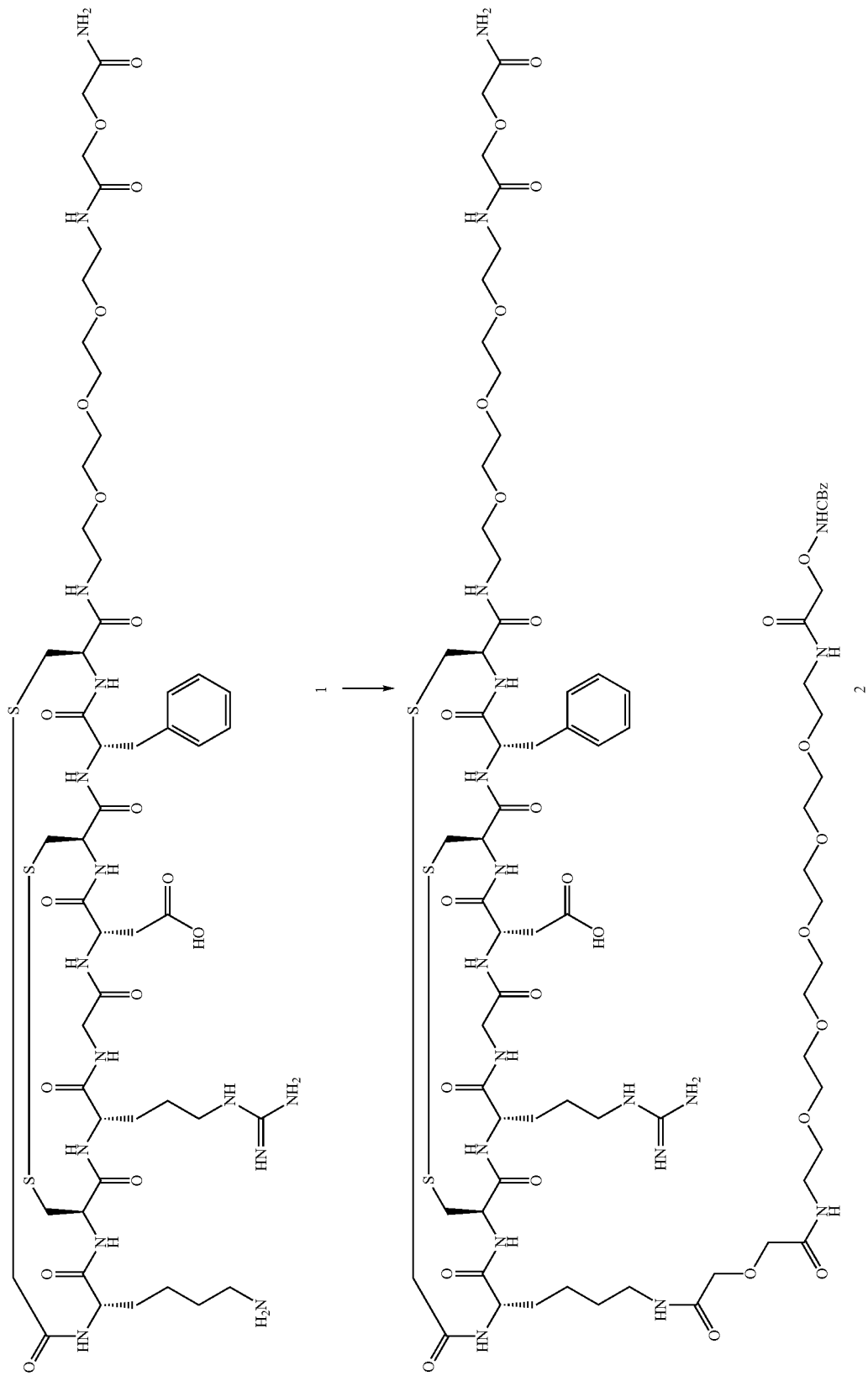

(a) 1,17-Diazido-3,6,9,12,15-pentaoxaheptadecane

A solution of dry hexaethylene glycol (25 g, 88 mmol) and methanesulphonyl chloride (22.3 g, 195 mmol) in dry THF (125 mL) was kept under argon and cooled to 0° C. in an ice/water bath. A solution of triethylamine (19.7 g, 195 mmol) in dry THF (25 mL) was added dropwise over 45 min. After 1 hr the cooling bath was removed and the reaction was stirred for another for 4 hrs. Water (55 mL) was then added to the mixture, followed by sodium hydrogencarbonate (5.3 g, to pH 8) and sodium azide (12.7 g, 195 mmol). THF was removed by distillation and the aqueous solution was refluxed for 24 h (two layers were formed). The mixture was cooled, ether (100 mL) was added and the aqueous phase was saturated with sodium chloride. The phases were separated and the aqueous phase was extracted with ether (4×50 mL). The combined organic phases were washed with brine (2×50 mL) and dried ($MgSO_4$). Filtration and evaporation of the solvent gave 26 g (89%) of a yellow oil. The product was used in the next step without further purification.

(b) 17-Azido-3,6,9,12,15-pentaoxaheptadecanamine

To a vigorously stirred suspension of 1,17-diazido-3,6,9,12,15-pentaoxaheptadecane (25 g, 75 mmol) in 5% HCl (200 mL) was added a solution of triphenylphosphine (19.2 g, 73 mmol) in ether (150 mL) over 3 hrs at room temperature. The reaction mixture was stirred for additional 24 hrs. The phases were separated and the aqueous phase was extracted with dichloromethane (3×40 mL). The aqueous phase was cooled in an ice/water bath and the pH was adjusted to 12 by addition of solid potassium hydroxide. The aqueous phase was concentrated and the product was taken up in dichloromethane (150 mL). The organic phase was dried ($Na_2SO_4$) and concentrated giving of 22 g (95%) of a yellow oil. The product was identified by electrospray mass spectrometry (ESI-MS) ($MH^+$ calculated: 307.19; found 307.4). The crude oil was used in the nest step without further purification.

(c) 23-Azido-5-oxo-6-aza-3,9,12,15,18,21-hexaoxatricosanoic acid

To a solution of 17-azido-3,6,9,12,15-pentaoxaheptadecanamine (15 g, 50 mmol) in dichloromethane (100 mL) was added diglycolic anhydride (Acros, 6.4 g, 55 mmol). The reaction mixture was stirred overnight. The reaction was monitored by ESI-MS analysis, and more reagents were added to drive the reaction to completion. The solution was concentrated to give a yellow residue which was dissolved in water (250 mL). The product was isolated from the aqueous phase by continuous extraction with dichloromethane over night. Drying and evaporation of the solvent gave a yield of 18 g (85%). The product was characterized by ESI-MS analysis ($MH^+$ calculated: 423.20; found 423.4). The product was used in the next step without further purification.

(d) 23-Amino-5-oxo-6-aza-3,9,12,15,18,21-hexaoxatricosanoic acid

23-Azido-5-oxo-6-aza-3,9,12,15,18,21-hexaoxatricosanoic acid (9.0 g, 21 mmol) was dissolved in water (50 mL) and reduced using $H_2(g)$-Pd/C (10%). The reaction was run until ESI-MS analysis showed complete conversion to the desired product ($MH^+$ calculated: 397.2; found 397.6). The crude product was used in the next step without further purification.

Photolabile protecting groups can be incorporated into the linker by reaction of the corresponding aminooxyacetic acid derivative, e.g. where the R groups studied are $CO_2Bn(CBz)$, $CH_2C_6H_4$-m-$NO_2$, $CO_2C_2 6H_4$-m-$NO_2$, $CO_2CH(Ph)C_6H_4$-o-$NO_2$, $SO_2Bn$, $CO_2C(Me)_2$-3,5-$(MeO)_2C_6H_3$, and $CO_2CH_2$-3,5-$(MeO)_2C_6H_3$.

(e) (CBz-aminooxy)acetyl-PEG(6)-diglycolic acid

A solution of dicyclohexycarbodiimide (515 mg, 2.50 mmol) in dioxane (2.5 mL) was added dropwise to a solution of (CBz-aminooxy)acetic acid (560 mg, 2.50 mmol) and N-hydroxysuccinimide (287 mg, 2.50 mmol) in dioxane (2.5 mL). The reaction was stirred at RT for 1 h and filtered. The filtrate was transferred to a reaction vessel containing a solution of 23-amino-5-oxo-6-aza-3,9,12,15,18,21-hexaoxatricosanoic acid (1.0 g, 2.5 mmol) and N-methymorpholine (278 µl, 2.50 mmol) in water (5 mL). The mixture was stirred at RT for 30 min. ESI-MS analysis showed complete conversion to the desired product.

The crude product was purified by preparative HPLC (column: Phenomenex Luna 5µ C18 (2) 250×21.20 mm, detection: 214 nm, gradient: 0-50% B over 60 min where $A=H_2O$/0.1% TFA and B=acetonitrile/0.1% TFA, flow rate: 10 mL/min).

The product was analyzed by HPLC (column: Phenomenex Luna 3µ C18 (2), 50×2.00 mm, detection: 214 nm, gradient: 0-50% B over 10 min where $A=H_2O$/0.1% TFA and B=acetonitrile/0.1% TFA, flow rate: 0.75 mL/min, Rt=5.52 min). Further confirmation was carried out by NMR analysis.

(f) Conjugation of (CBz-aminooxy)acetyl-PEG(6)-diglycolic acid to Compound 1

(CBz-aminooxy)acetyl-PEG(6)-diglycolic acid (0.15 mmol, 90 mg) and PyAOP (0.13 mmol, 68 mg) were dissolved in DMF (2 mL). N-methylmorpholine (0.20 mmol, 20 µL) was added and the mixture was stirred for 10 min. A solution of Compound 1 (0.100 mmol, 126 mg) and N-methylmorpholine (0.20 mmol, 20 µL) in DMF (4 mL) was added and the reaction mixture was stirred for 25 min. Additional N-methylmorpholine (0.20 mmol, 20 µL) was added and the mixture was stirred for another 15 min. DMF was evaporated in vacuo and the product was taken up in 10% acetonitrile-water and purified by preparative HPLC (column: Phenomenex Luna 5µ C18 (2) 250×21.20 mm, detection: UV 214 nm, gradient: 5-50% B over 40 min where $A=H_2O$/0.1% TFA and B=acetonitrile/0.1% TFA, flow rate: 10 mL/min,) affording 100 mg semi-pure product which could be further purified where TFA was replaced by HCOOH (gradient: 0-30% B, otherwise same conditions as above). The product was analysed by HPLC (column: Phenomenex Luna 3µ C18 (2) 50×2 mm, detection: UV 214 nm, gradient: 0-30% B over 10 min where $A=H_2O$/0.1% HCOOH and B=acetonitrile/0.1% HCOOH, flow rate: 0.3 mL/min, Rt: 10.21 min). Further product characterisation was carried out using ESI-MS.

Removal of a Photolabile Protecting Group from an Aminoxy Group in Preparing a Radiolabeled Peptide-Based Compound

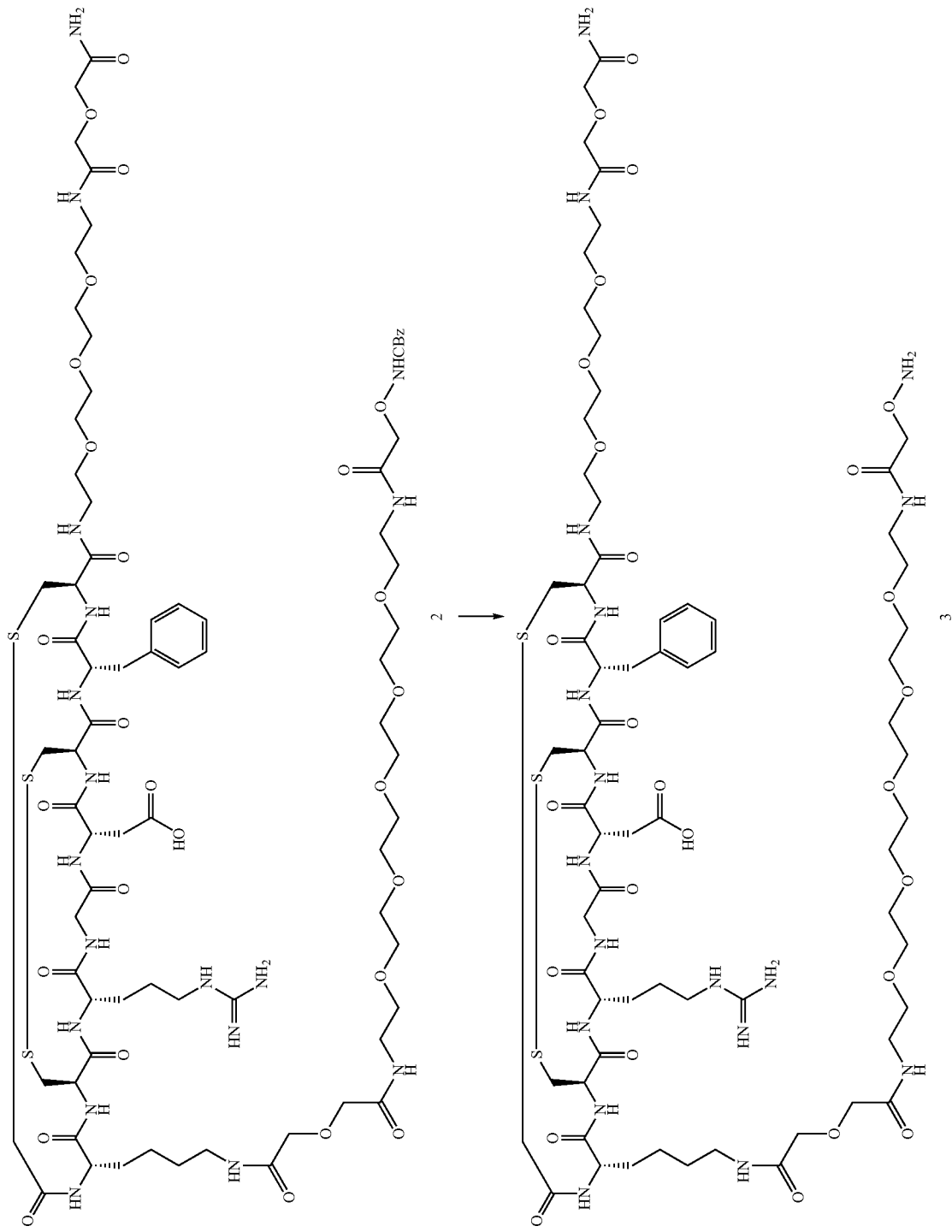

The R groups studied in 2 are $CO_2Bn(CBz)$, $CH_2C_6H_4$-m-$NO_2$, $CO_2C_2 6H_4$-m-$NO_2$, $CO_2CH(Ph)C_6H_4$-o-$NO_2$, $SO_2Bn$, $CO_2C(Me)_2$-3,5-$(MeO)_2C_6H_3$, and $CO_2CH_2$-3,5-$(MeO)_2C_6H_3$ wherein 2 was reacted with light generated from a medium- or high-pressure mercury lamp with an automated cut-off filter with a wavelength between 200-600 nm. For precise control of the wavelength, a Rayonet™ or Luzchem™ photoreactor lamp equipped with monochromatic bulbs at 254, 300, 350, or 419 nm is required. This reaction was carried out in connection with an automated radiosynthesis apparatus wherein compound 3 was formed.

Radiosynthesis of $^{18}$F-Fluorobenzaldehyede $^{18}$F-Fluoride (up to 370 MBq) is azeotropically dried in the presence of Kryptofix 222 (5 mg in 0.5 ml acetonitrile) and potassium carbonate (50 μl 0.1M solution in water) by heating under $N_2$ to 110° C. for 20 mins. During this time 3×0.5 ml acetonitrile are added and evaporated. After cooling to <40° C., a solution of trimethylammonium benzaldehyde triflate (1 mg in 0.4 ml DMSO) is added. The reaction vessel is sealed and heated to 90° C. for 15 mins to effect labelling. The crude reaction mixture is cooled to room temperature and diluted by addition of water. The mixture will be passed sequentially through ion exchange cartridges (preconditioned with ethanol (or acetonitrile) and water) and eluted in an acetonitrile/water mixture. The eluate will be concentrated using a C18 Seppak, and the fluorobenzaldehyde will be eluted in acetonitrile.

Conjugation of Compound 3 and 3-$^{18}$F-Fluorobenzaldehyde

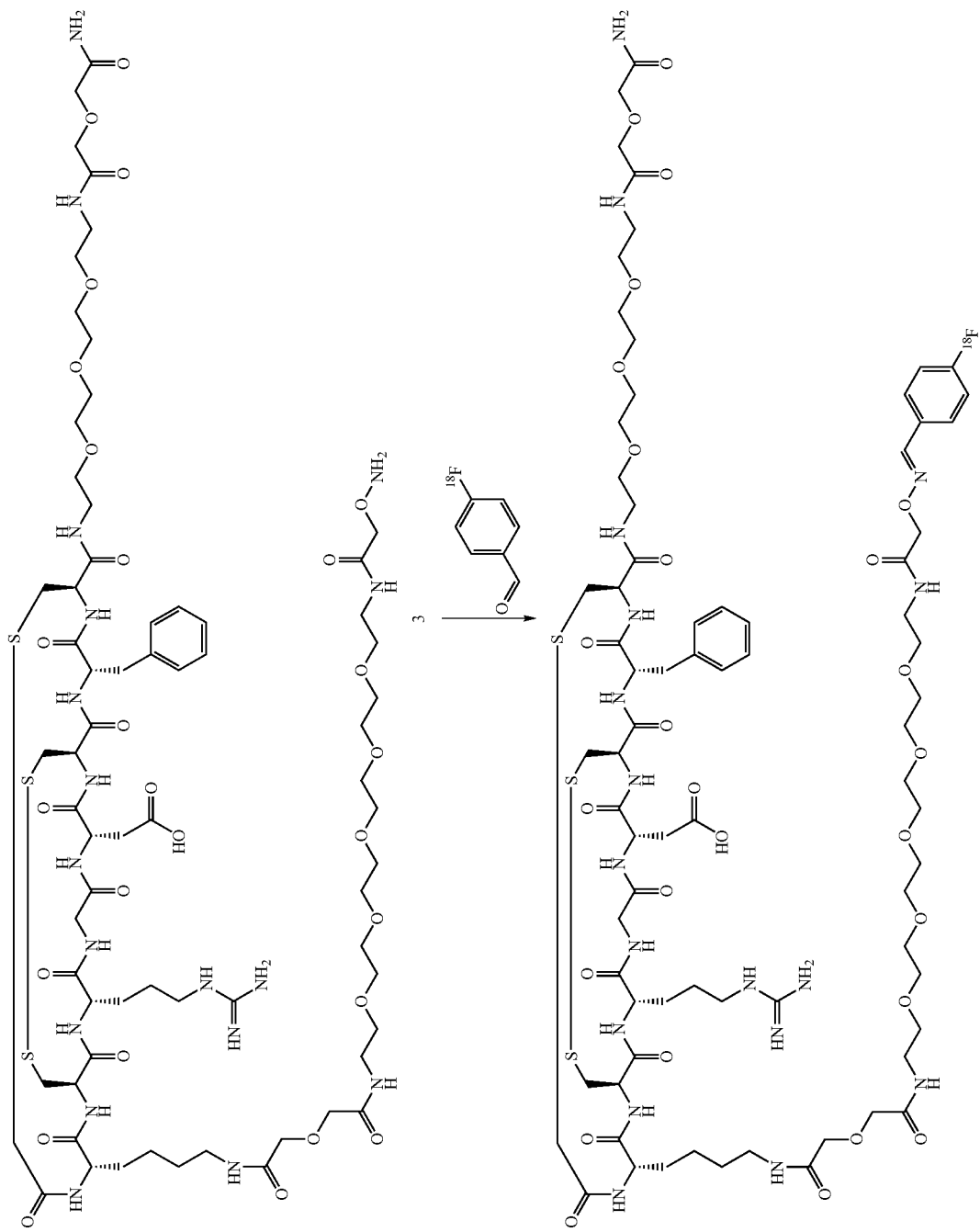

Compound 3 is treated with 5% water in TFA for 5 mins at room temperature. The solvents are then removed by evaporation under vacuum. The peptide is redissolved in 0.1M NH$_4$OAc buffer, pH4 (0.5 ml) and combined with 4-$^{18}$F-fluorobenzaldehyde in the reaction vessel. The reaction vessel is sealed and heated to 70° C. for 15 mins to effect conjugation. After cooling to room temperature, the product is obtained by preparative radio HPLC (as described for method 1) or by SPE.

SPECIFIC EMBODIMENTS, CITATION OF REFERENCES

The present invention is not to be limited in scope by specific embodiments described herein. Indeed, various modifications of the inventions in addition to those described herein will become apparent to those skilled in the art from the foregoing description and accompanying figures. Such modifications are intended to fall within the scope of the appended claims.

Various publications and patent applications are cited herein, the disclosures of which are incorporated by reference in their entireties.

What is claimed is:

1. A method of preparing a compound of formula (II) comprising the steps;
   (i) adding a photolabile protecting group, R, to an aminoxy group to give formula (I)

   (I)

wherein the R denotes CO$_2$Bn(CBz), CH$_2$C$_6$H$_4$-m-NO$_2$, CO$_2$C$_6$H$_4$-m-NO$_2$, CO$_2$CH(Ph)C$_6$H$_4$-o-NO$_2$, SO$_2$Bn, CO$_2$C(Me)$_2$-3,5-(MeO)$_2$C$_6$H$_3$, or CO$_2$CH$_2$-3,5-(MeO)$_2$C$_6$H$_3$, Bn denotes benzyl group, CBz denotes benzyloxycarbonyl group, and Ph denotes a phenyl,

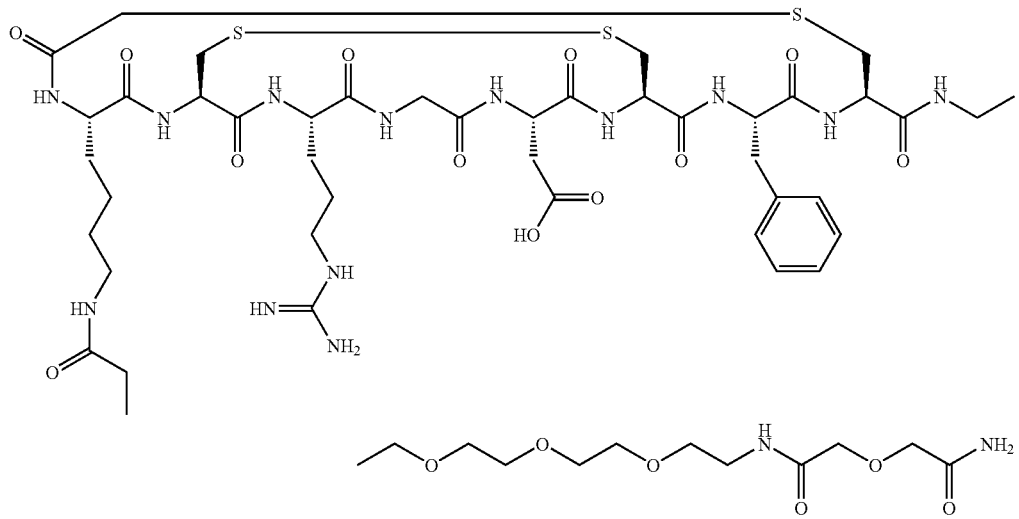

(ii) illuminating compound (I) with a light in an automated radiosynthesis apparatus to form a compound of formula (II),

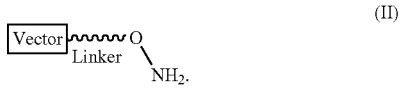
   (II)

2. The method according to claim 1, wherein the light of a specified wavelength is from about 200 nm to about 600 nm and more preferably about 220 nm to about 380 nm to liberate the aminoxy precursor.

3. The method according to claim 2, wherein the light used herein is produced from lamps.

4. The method according to claim 3, wherein the lamps are of medium or high pressure Hg or Hg—Xe lamps fitted with filters to direct light of a desired wavelength.

5. The method according to claim 1, wherein R is preferably CO$_2$Bn (CBz).

6. A method as claimed in claim 1 wherein the vector is a peptide based vector.

7. A method as claimed in claim 1 wherein the vector is an RGD-based peptide having affinity for angiogenesis.

8. A method as claimed in claim 1 wherein the linker is based on a PEG building block.

9. A method as claimed in claim 1 wherein compound of formula (I) is a compound of formula (IV)

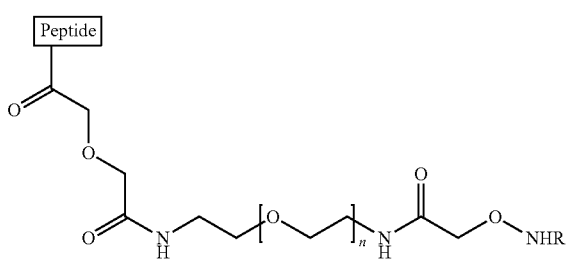

wherein n denotes a positive integer of 3 to 5 and n is preferably 5, wherein the peptide denotes

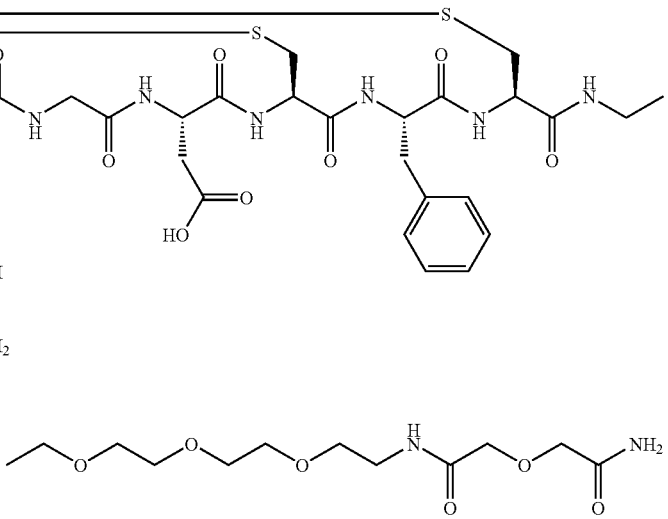

and R denotes CO$_2$Bn(CBz), CH$_2$C$_6$H$_4$-m-NO$_2$, CO$_2$C$_2$6H$_4$-m-NO$_2$, CO$_2$CH(Ph)C$_6$H$_4$-o-NO$_2$, SO$_2$Bn, CO$_2$C(Me)$_2$-3,5-(MeO)$_2$C$_6$H$_3$, or CO$_2$CH$_2$-3,5-(MeO)$_2$C$_6$H$_3$, wherein Bn denotes benzyl group, CBz denotes benzyloxycarbonyl group, and Ph denotes a phenyl.

10. A method of preparing a compound of formula (III) comprising the steps: reacting a compound of formula (II)

23

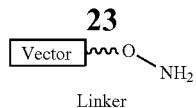
Linker with an $^{18}$F-fluoride synthon to prepare the compound of formula (III)

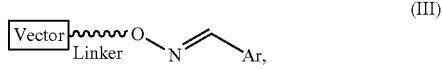
(III)

wherein Ar denotes an aryl function of the formula

24

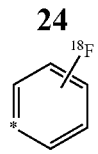

and * denotes the attachment to the imino function.

11. A method as claimed in claim 10 wherein the $^{18}$F-fluoride synthon is $^{18}$F-radiolabelled benzaldehyde.

12. A method as claimed in claim 10 for preparing a compound of formula (V)

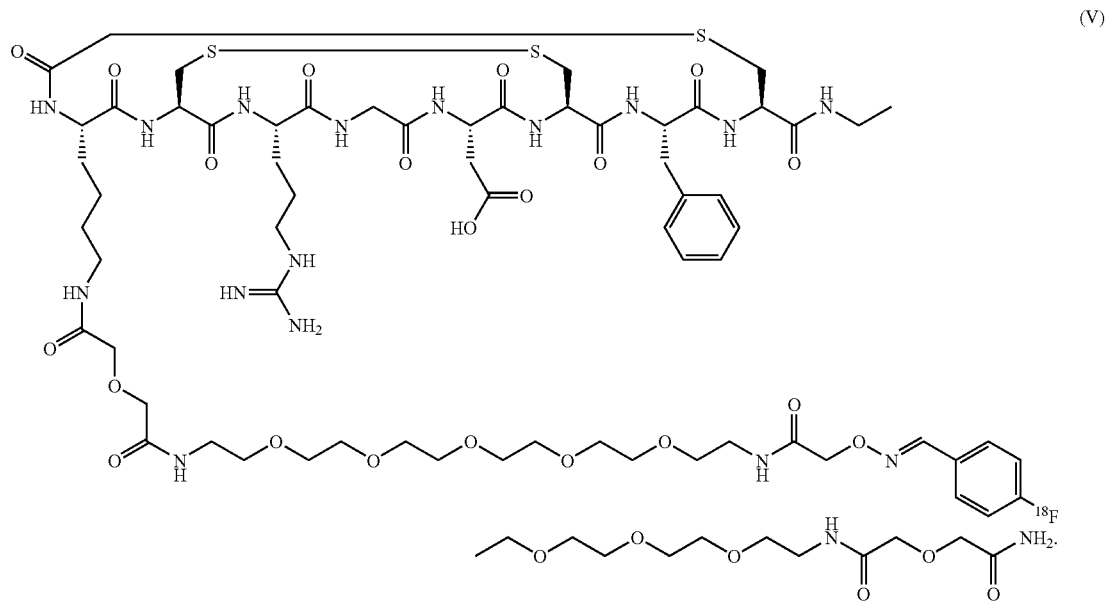
(V)

13. A compound of formula (I)

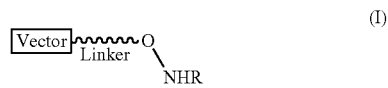
(I)

wherein the R denotes $CO_2Bn(CBz)$, $CH_2C_6H_4$-m-$NO_2$, $CO_2C_6H_4$-m-$NO_2$, $CO_2CH(Ph)C_6H_4$-o-$NO_2$, $SO_2Bn$, $CO_2C(Me)_2$-3,5-$(MeO)2C_6H_3$, or $CO_2CH_2$-3,5-(MeO)$2C_6H_3$, Bn denotes benzyl group, CBz denotes benzyloxycarbonyl group, and Ph denotes a phenyl.

14. A compound formula (I) of claim 13, wherein the vector comprises the fragment

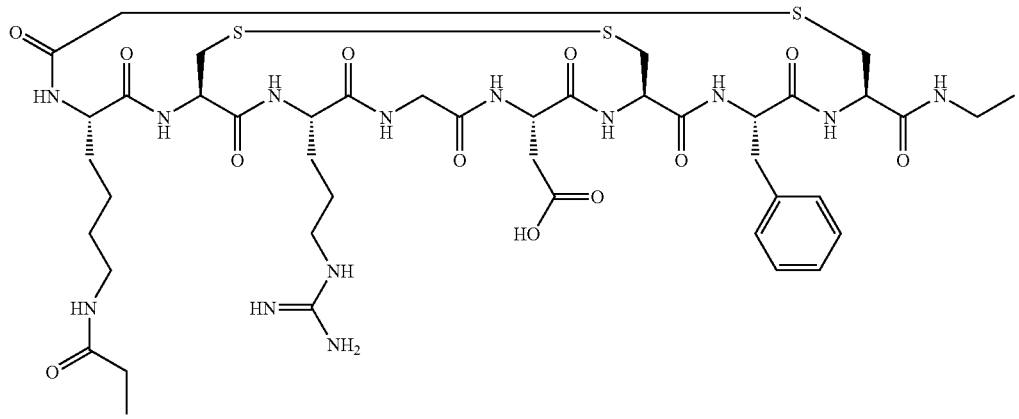

-continued
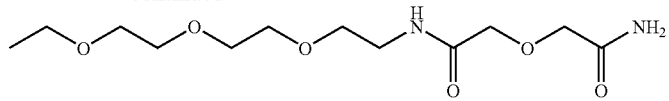
15. A compound of formula (III)
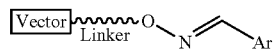
(III)
wherein Ar denotes an aryl function of the formula
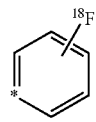
and * denotes the attachment to the imino function, wherein the vector is Arg-Gly-Asp peptide or an analogue thereof.
* * * * *